United States Patent
Kolari et al.

(10) Patent No.: US 9,278,874 B2
(45) Date of Patent: Mar. 8, 2016

(54) PREVENTION OF STARCH DEGRADATION IN PULP, PAPER OR BOARD MAKING PROCESSES USING ZINC IONS AND AN OXIDIZING BIOCIDE

(71) Applicant: KEMIRA OYJ, Helsinki (FI)

(72) Inventors: Marko Kolari, Vantaa (FI); Jaakko Ekman, Vantaa (FI); Satu Ikävalko, Espoo (FI)

(73) Assignee: KEMIRA OYJ, Helsinki (FI)

( * ) Notice: Subject to any disclaimer, the term of this patent is extended or adjusted under 35 U.S.C. 154(b) by 0 days.

(21) Appl. No.: 14/348,070

(22) PCT Filed: Sep. 28, 2012

(86) PCT No.: PCT/EP2012/069228
§ 371 (c)(1),
(2) Date: Mar. 28, 2014

(87) PCT Pub. No.: WO2013/045638
PCT Pub. Date: Apr. 4, 2013

(65) Prior Publication Data
US 2014/0242191 A1    Aug. 28, 2014

Related U.S. Application Data

(60) Provisional application No. 61/541,509, filed on Sep. 30, 2011.

(51) Int. Cl.
| | |
|---|---|
| *A01N 25/02* | (2006.01) |
| *C02F 1/50* | (2006.01) |
| *A01N 65/00* | (2009.01) |
| *A61Q 17/00* | (2006.01) |
| *A01N 59/16* | (2006.01) |
| *D21H 21/36* | (2006.01) |
| *C02F 103/28* | (2006.01) |

(52) U.S. Cl.
CPC . *C02F 1/50* (2013.01); *A01N 59/16* (2013.01); *A01N 65/00* (2013.01); *A61Q 17/005* (2013.01); *D21H 21/36* (2013.01); *C02F 1/505* (2013.01); *C02F 2103/28* (2013.01)

(58) Field of Classification Search
CPC .......................... A01N 65/00; A61Q 17/005
See application file for complete search history.

(56) References Cited

U.S. PATENT DOCUMENTS 7,455,851 B1 * 11/2008 Nelson et al. ................ 424/406
9,155,310 B2 * 10/2015 Agrawal et al.

FOREIGN PATENT DOCUMENTS

| EP | 2016827 | 1/2009 |
|---|---|---|
| WO | 02052935 | 7/2002 |

(Continued)

OTHER PUBLICATIONS

Notification Concerning Transmittal of International Preliminary Report on Patentability; dated Apr. 10, 2014; Application No. PCT/EP2012/069228; WIPO, Geneva Switzerland; 7 pages.

(Continued)

*Primary Examiner* — Carlos Azpuru
(74) *Attorney, Agent, or Firm* — Thomas Horstemeyer, LLP

(57) ABSTRACT

The invention relates to biocidal systems comprising zinc ions and an oxidizing or non-oxidizing biocide, their use, and methods for preventing or decreasing starch degradation in starch-containing process waters from pulp, paper or board production processes.

5 Claims, 2 Drawing Sheets

(56) References Cited

FOREIGN PATENT DOCUMENTS

| WO | 2006093556 |   | 9/2006 |
| WO | 2007026004 |   | 3/2007 |
| WO | 2007088172 |   | 8/2007 |
| WO | 2007088172 | * | 9/2007 |

OTHER PUBLICATIONS

Irshad M. et al.: "Effect of Zn<2+> on plant alpha-amylases in vitro", Phytochemistry, Pergamon Press, GB, vol. 20, No. 9, Jan. 1, 1981.

International Search Report and Written Opinion, mailed Mar. 12, 2013.

* cited by examiner

US 9,278,874 B2

PREVENTION OF STARCH DEGRADATION IN PULP, PAPER OR BOARD MAKING PROCESSES USING ZINC IONS AND AN OXIDIZING BIOCIDE

CROSS-REFERENCE TO RELATED APPLICATION

This application is the 35 U.S.C. §371 national stage of PCT Application No. PCT/EP2012/069228, filed Sep. 28, 2012, which is herein incorporated by reference in its entirety and which also claims priority to, and the benefit of U.S. patent application No. 61/541,509, filed Sep. 30, 2011, which is herein incorporated by reference in its entirety.

FIELD OF THE DISCLOSURE

This application relates to biocides and more particularly to biocidal systems comprising Zn ions and biocides, their use, and methods for preventing or decreasing starch degradation in pulp, paper, or board making processes.

BACKGROUND

It is well known in the pulp, paper or board making industry to apply oxidizing or non-oxidizing biocides to control microbial growth. Examples of commonly used non-oxidizing biocides are glutaraldehyde, 2,2-dibromo-3-nitrilopropionamide (DBNPA), 2-bromo-2-nitropropane-1,3-diol (Bronopol), quaternary ammonium compounds, carbamates, 5-chloro-2-methyl-4-isothiazolin-3-one (CMIT), and 2-methyl-4-isothiazolin-3-one (MIT). Typical examples of commonly used oxidizing biocides are chlorine, hypochlorite salts, hypochlorous acid, chlorinated isocyanurates, bromine, hypobromite salts, hypobromous acid, bromine chloride, chlorine dioxide, ozone, hydrogen peroxide, or peroxy compounds.

A specific application of biocides is the control of starch degradation in process waters of the paper industry. Starch is a widely used additive in paper making. Actually paper making is the largest non-food usage of starch. For example, in the wet end of a paper machine, starch is used to improve paper strength. In the dry end of a paper machine, starch is used for coating the paper in a process called surface sizing. This gives paper additional strength and better printing properties.

Amylase is an enzyme that catalyzes degradation of starch. It is produced by many microorganisms, both fungi and bacteria, and is also present for example in human saliva. Amylase enzymes are divided into three groups: $\alpha$-, $\beta$- and $\gamma$-amylases. They all hydrolyse $\alpha$-1,4-glycosidic bonds that link together glucose units of starch molecule. $\beta$-amylase can break only the second $\alpha$-1,4-glycosidic bond, yielding into two glucose units (maltose). $\alpha$-amylase can attack any bonds in the starch molecule and thus is often faster acting than $\beta$-amylase. $\gamma$-amylase cleaves one glucose unit at the time and is most efficient in acidic environments.

Process waters in the paper industry can contain microorganisms which can produce amylase enzymes that degrade starch and cause loss of the functionality of added starch additive. This will lead either to paper quality issues, or alternatively force to increase starch dosages thus creating unwanted additional costs.

Current practices in controlling starch degradation have been inadequate in efficacy or have required economically unfeasible high biocide dosages. Especially when process water with high amylase activity is used for pulping of recycled fiber, or in re-pulping of dry broke of a paper or board machine, degradation of starch is easily taking place and the benefits of the starch already included in the fibrous material from recycled paper (which contains plenty of starch from the original production process) is lost.

WO 2012/025228 A1 discloses a method for manufacturing paper, wherein a cellulosic material containing starch is treated with biocides, followed by adding an ionic polymer and an auxiliary ionic polymer, both polymers having different average molecular weight and different ionicity.

DESCRIPTION

Surprisingly, it has been found that when combining Zn ions (e.g., via a Zn ion source compound) with one or more biocides, an enhanced prevention or reduction of starch degradation can be obtained. Although not intending to be bound by theory, it is believed that this is due to two different mechanisms, one mechanism inhibiting existing amylase activity and the other mechanism preventing the production of new amylase by microorganisms, giving a synergistic impact. The new combination provides a synergistic end result effectively decreasing or preventing starch degradation.

Accordingly, the present disclosure relates to a biocidal composition comprising zinc ions (e.g., via a zinc ion source compound) and a biocide. In an embodiment, the biocide can be an oxidizing biocide, or a non-oxidizing biocide, except zinc pyrithione or 1,2-benzoisothiazolin-3-one and zinc pyrithione (i.e., non-oxidizing biocide excludes zinc pyrithione or 1,2-benzoisothiazolin-3-one and zinc pyrithione for biocidal composition embodiments). Preferably, the biocide in the biocidal composition of the present disclosure is an oxidizing biocide.

An embodiment of the present invention includes a biocidal system, biocidal combination or biocidal mixture that includes the individual components of zinc ions and a biocide, which can form an in situ biocidal composition. An embodiment of the present disclosure includes a biocidal system that includes a combination of zinc ions and a biocide. In an embodiment, the biocide is an oxidizing biocide or a non-oxidizing biocide, preferably the biocide is an oxidizing biocide. A proviso of the biocidal system of the invention is that the non-oxidizing biocide does not include zinc pyrithione or both 1,2-benzoisothiazolin-3-one and zinc pyrithione.

The present disclosure and invention further relates to a method for controlling starch degradation in starch-containing process waters from pulp, paper or board production, comprising treating the process water with a biocidal system comprising zinc ions and a biocide. In addition, the present disclosure and invention relates to the use of a biocidal system comprising zinc ions and a biocide, for treatment of starch-containing process waters from pulp, paper or board production. The biocide can be an oxidizing or non-oxidizing biocide. The biocidal system is used in an amount effective to decrease or prevent starch degradation. In regard to methods for controlling starch degradation and/or treating process waters with the biocidal system, the non-oxidizing biocide can include zinc pyrithione or both zinc pyrithione and 1,2-benzoisothiazolin-3-one. It is also possible that either zinc pyrithione or both zinc pyrithione and 1,2-benzoisothiazolin-3-one are used as the biocidal system in the methods of the invention.

Preferred embodiments of the invention are described in the description hereinafter, the examples, the claims and the figures.

DRAWINGS

Figure 1:
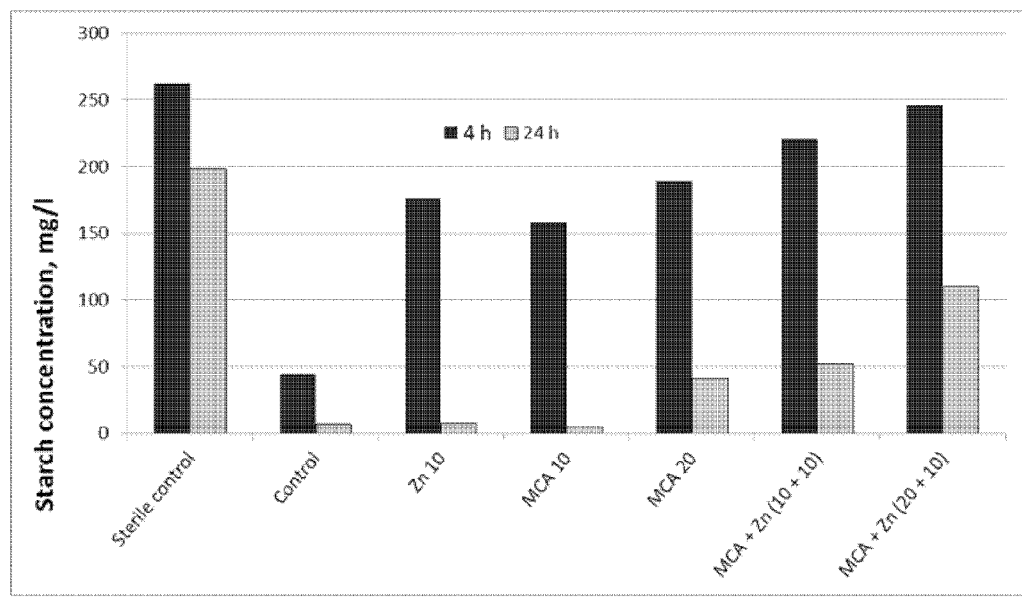
FIG. 1 shows protection of starch from degradation using zinc and monochloramine (MCA), wherein two contact times, 4 h and 24 h, were used. Zinc concentration is given as mg of $Zn^{2+}$ ions per liter and MCA concentrations are given as mg of active chlorine per liter.

It is known that Zn ions can inhibit the enzyme amylase (see, for example: Irshad et. al. 1981: *Effect of $Zn^{2+}$ on plant α-amylases in vitro*. Phytochemistry. 20:2123-2126). According to the present disclosure Zn ions can be used in combination with a biocide, which yields an unexpected synergistic effect in preventing or decreasing (e.g., about a 90% decrease or more, about a 80% decrease or more, about a 70% decrease or more, about a 60% decrease or more, about a 50% decrease or more, about a 40% decrease or more, about at 30% decrease or more, or about a 20% decrease or more, relative to a system not including the Zn and biocide) starch degradation. E.g., degradation can include breaking down the starch into smaller components, e.g., reducing the amount of starch present by about 10% or more, about 20% or more, about 30% or more, about 40% or more, about 50% or more, about 60% or more, about 70% or more, about 80% or more, or about 90% or more, relative to not including the Zn and biocide.

In an exemplar embodiment, the source of the Zn ions can be an inorganic or organic zinc compound, in particular an inorganic or organic zinc salt. Preferably, the zinc ion source is selected from $ZnBr_2$, $ZnCl_2$, $ZnF_2$, $ZnI_2$, ZnO, $Zn(OH)_2$, ZnS, ZnSe, ZnTe, $Zn_3N_2$, $Zn_3P_2$, $Zn_3As_2$, $Zn_3Sb_2$, $ZnO_2$, $ZnH_2$, $ZnC_2$, $ZnCO_3$, $Zn(NO_3)_2$, $Zn(ClO_3)_2$, $ZnSO_4$, $Zn_3(PO_4)_2$, $ZnMoO_4$, $ZnCrO_4$, $Zn(AsO_2)_2$, $Zn(AsO_4)_2$, $Zn(O_2CCH_3)_2$, or zinc metal, or a combination thereof. Preferably, an inorganic zinc salt is used. Preferred are the zinc salts $ZnCl_2$, $ZnBr_2$, $ZnSO_4$ and $Zn(O_2CCH_3)_2$, most preferably $ZnCl_2$ is used.

In an exemplar embodiment, the non-oxidizing biocides can include glutaraldehyde, 2,2-dibromo-3-nitrilopropionamide (DBNPA), 2-bromo-2-nitropropane-1,3-diol (Bronopol), quaternary ammonium compounds, carbamates, 5-chloro-2-methyl-4-isothiazolin-3-one (CMIT), 2-methyl-4-isothiazolin-3-one (MIT), 1,2-dibromo-2,4-dicyanobutane, bis(trichloromethyl)sulfone, 2-bromo-2-nitrostyrene, 4,5-dichloro-1,2-dithiol-3-one, 2-n-octyl-4-isothiazolin-3-one, 1,2-benzisothiazolin-3-one, ortho-phthaldehyde, quaternary ammonium compounds (="quats"), such as n-alkyl dimethyl benzyl ammonium chloride, didecyl dimethyl ammonium chloride (DDAC) or alkenyl dimethylethyl ammonium chloride, guanidines, biguanidines, pyrithiones, 3-iodopropynyl-N-butylcarbamate, phosphonium salts, such as tetrakis hydroxymethyl phosphonium sulfate (THPS), dazomet, 2-(thiocyanomethylthio) benzothiazole, methylene bisthiocyanate (MBT), and a combination thereof. Preferred non-oxidizing biocides are selected from glutaraldehyde, 2,2-dibromo-3-nitrilopropionamide (DBNPA), 2-bromo-2-nitropropane-1,3-diol (Bronopol), quaternary ammonium compounds, carbamates, 5-chloro-2-methyl-4-isothiazolin-3-one (CMIT) and 2-methyl-4-isothiazolin-3-one (MIT). Most preferably, glutaraldehyde is used.

In an exemplar embodiment, the oxidizing biocides can include an oxidant selected from chlorine, alkali and alkaline earth hypochlorite salts, hypochlorous acid, chlorinated isocyanurates, bromine, alkali and alkaline earth hypobromite salts, hypobromous acid, bromine chloride, chlorine dioxide, ozone, hydrogen peroxide, peroxy compounds, such as peracetic acid, performic acid, percarbonate or persulfate salts, halogenated hydantoins, e.g., monohalodimethylhydantoins such as monochlorodimethylhydantoin, or dihalodimethylhydantoins such as chlorobromodimethylhydantoin, mono chloramines, monobromamines, dihaloamines, trihaloamines, or a combination thereof. The oxidant can be combined with an optionally substituted N-hydrogen compound. Particular N-hydrogen compounds are selected from ammonium salts, ammonia, urea, hydantoin, isothiazoline-1,1-dioxide, ethanolamine, pyrrolidine, 2-pyrrolidone, ethylene urea, N-methylolurea, N-methylurea, acetylurea, pyrrole, indole, formamide, benzamide, acetamide, imidazoline, or morpholine. Other suitable N-hydrogen compounds are disclosed in WO 2012/101051 A1. Particularly suitable oxidizing biocides can include ammonium salts reacted with an oxidant, for example, ammonium bromide or ammonium sulfate, or any other ammonium salt, which is reacted with an oxidant, e.g., hypochlorite, or urea reacted with an oxidant, e.g., hypochlorite. Preferred oxidizing biocides are selected from monochloramine (MCA), chlorine dioxide, performic acid (PFA), peracetic acid, alkali and alkaline earth hypochlorite salts, and N-hydrogen compounds combined with an oxidant. Most preferably, monochloramine (MCA), chlorine dioxide, performic acid, or a N-hydrogen compound combined with an oxidant, e.g. urea reacted with an oxidant, is used.

It is also possible to use in the methods or the processes of the disclosure zinc pyrithione. Zinc pyrithione contains Zn ions and is a non-oxidizing biocide. In the present disclosure zinc pyrithione can be used as a zinc salt.

Amounts or quantities are herein defined in ppm or mg/l, wherein ppm (parts per million) means the same unit as mg/l, so that those units are interchangeably used. The amounts or quantities herein defined for the biocides refer to the active ingredient of the biocide, except for those halogen-based oxidizing biocides separately mentioned, for which the amounts of biocides refer to the concentration of total active chlorine. In this case, the common scale for the oxidative power of the oxidizing biocide is its activity compared to chlorine gas ($Cl_2$). Total active chlorine means the concentration of elemental chlorine that is stoichiometrically equivalent to the concentration of active halogen in a given system. Thus, for example, 100 mg/l of a commercial hypochlorite product with nominal sodium hypochlorite concentration of 15% (w/w), corresponding to a stoichiometric concentration of about 14.2 mg/l of total active chlorine ($Cl_2$), was added in process water. Activity of such a product is always lowering in time, and when measured the added quantity of hypochlorite product was 12 mg/l as total active chlorine ($Cl_2$), meaning that this hypochlorite addition had the same oxidative power as would addition of 12 mg/l of elemental chlorine have had.

The amounts to be used for the zinc ions and the biocide depend on the starch-containing process waters to be treated and the type of the biocide used.

In an exemplar embodiment, the Zn source can be used in amount to provide about 1 to 1000 ppm, in particular about 10 to 500 ppm, more preferably about 20 to 200 ppm, more preferably about 50 to 150 ppm $Zn^{2+}$ ions in the starch-containing process water.

In a preferred embodiment, the zinc source is used in an amount to provide about 0.1 to 1000 mg/l, in particular about 0.5 to 1000 mg/l, more preferably about 2 to 800 mg/l, zinc ions in the starch-containing waters to be treated. Further preferred amounts are about 2 to 500 mg/l, in particular about 2 to 300 mg/l, preferably about 3 to 100 mg/l, most preferably 5 to 50 mg/l, zinc ions.

In an exemplar embodiment, the oxidizing biocide is preferably used in an amount to provide a concentration of about 0.1 to 100 ppm, in particular about 0.1 to 50 ppm, more preferably about 0.1 to 15 ppm, more preferably about 0.5 to 10 ppm, based on the active compound content of the oxidizing biocide in the starch-containing process water. In an embodiment where the oxidizing biocide contains chlorine (by active compound content is understood a total active chlorine compound) of about 0.1 to 100 ppm, in particular about 0.1 to 50 ppm, more preferably about 0.1 to 15 ppm, more preferably about 0.5 to 10 ppm in the starch-containing process water.

In a preferred embodiment, the oxidizing biocide is used in an amount to provide a concentration of about 0.1 to 1000 mg/l, in particular about 0.5 to 500 mg/l, more preferably about 0.5 to 100 mg/l, even more preferably about 0.7 to 50 mg/l, most preferably about 1 to 20 mg/l, of the active ingredient of the oxidizing biocide, in the starch-containing waters to be treated.

In an exemplar embodiment, the non-oxidizing biocide is preferably used in an amount of about 0.1 to 1000 ppm, preferably about 1 to 500 ppm, more preferably about 5 to 100 ppm in the starch-containing process water.

In a preferred embodiment, the non-oxidizing biocide is used in an amount to provide a concentration of about 0.1 to 1000 mg/l, in particular about 0.5 to 500 mg/l, more preferably about 0.5 to 200 mg/l, more preferably about 1 to 100 mg/l, most preferably about 2 to 50 mg/l, of the active ingredient of the non-oxidizing biocide, in the starch-containing waters to be treated.

In the present disclosure ppm means weight of active compound per volume of the process water. Process water includes the solid matter.

In an exemplar embodiment, the Zn ions and the oxidizing biocide can be used in a ratio of about 1:1 to 100:1. In a preferred embodiment of the biocidal system, the zinc ions and the oxidizing biocide are present in a ratio of about 1:10 to 100:1, preferably about 1:5 to 20:1, more preferably about 1:2 to 5:1, based on the weight of the components.

In an exemplar embodiment, the zinc ions and the non-oxidizing biocide can be used in a ratio of about 1:10 to 10:1. In a preferred embodiment of the biocidal system, the zinc ions and the oxidizing biocide are present in a ratio of about 1:20 to 20:1, preferably about 1:10 to 10:1, more preferably about 1:5 to 5:1, based on the weight of the components.

If zinc pyrithione is used, it is preferably used in an amount of about 0.1 to 1000 ppm, preferably about 1 to 500 ppm, more preferably about 5 to 100 ppm, in the starch-containing process water.

The zinc ions and the biocide can be continuously, intermittently or alternately added to the starch-containing waters to be treated. The zinc ions and the biocide can be added simultaneously or sequentially to the waters to be treated. In case of sequential addition, the biocide can be added prior to the addition of the zinc ions, or the zinc ions can be added prior to the addition of the biocide. According to requirements, it is also possible to add one component continuously and the other component intermittently.

In an exemplar embodiment, the components of the biocidal system can be added simultaneously or sequentially to the process water. If added sequentially, the time between the single additions should preferably not exceed, about 180 minutes, preferably about 60 minutes, more preferably about 30 minutes, more preferably about 20 minutes, more preferably about 10 minutes, or more preferably about 5 minutes. In an embodiment, the Zn is added first, and in another embodiment, the Zn is added second. In an embodiment, the components can be mixed together and added all at once or in portions. In an embodiment, the components are added separately all at once or in portions. In an embodiment, a portion of the Zn is added and then a portion of the biocide is added and this can be alternated in the same or different time frames until all of the Zn and biocide are added. In an embodiment, a portion of the biocide is added and then a portion of the Zn is added and this can be alternated in the same or different time frames until all of the Zn and biocide are added.

The present disclosure can be used for process waters from the pulp, paper and board producing industry, which process waters contain starch. In general, the biocidal system can be added to a position containing starch and including components that may degrade the starch. The biocidal system can be added to the broke system, pulp, pulp storage tanks, to the water entering the pulper or into the pulper, water storage tanks, or pipe line before the broke or pulp storage tanks. In particular, the biocidal system can be used in pulping of starch-containing recycled fiber and/or in broke systems. Reduced starch consumption would gain paper makers a significant saving in starch consumption, reduce runnability problems and increase paper quality.

The invention also relates to the use of a biocidal system comprising zinc ions and a biocide, for treatment of starch-containing process waters from pulp, paper or board production. The zinc ions and the biocide can be the same as defined above. The biocidal system can be added to a broke system, pulp, pulp storage tanks, to the water entering the pulper or into the pulper, water storage tanks, or pipe line before the broke or pulp storage tanks.

The invention further relates to a method of inhibiting existing amylase activity, and/or preventing or reducing the production of new amylase by microorganisms in starch-containing fluid, wherein the method comprises treating the fluid with zinc ions and a biocide. The zinc ions and the biocide can be the same as defined above. The starch-containing fluid can be the same as the above-defined process water from pulp, paper or board production.

The invention is further illustrated by the following examples, which show preferred embodiments, without limiting the scope of protection.

EXAMPLE 1

Prevention of starch degradation was studied using an oxidizing biocide (monochloramine, MCA) and zinc. Head box stock from packaging board mill, stored at +4° C. after collecting, was amended with 0.8 g/l cooked starch and incubated overnight at 45° C. with 150 rpm shaking to induce the growth of starch degrading bacteria. The stock was divided into 30 ml portions and appropriate amounts of zinc ($Zn^{2+}$ from zinc chloride) and MCA were added together with a new starch addition (400 mg/l). After 4 h and 24 h incubation (+45° C., 150 rpm) the remaining starch was quantified using iodine staining (Lugol-solution) at 590 nm. An external standard curve was used to convert absorbance values into starch amounts.

Table 1 below and FIG. 1 show that when no bacteria were present (sterile control) the measurable starch concentration was about 250 mg/l after 4 h and 200 mg/l after 24 h. The rest of the starch had probably retained onto fibers. In non-treated control most of the starch had been degraded already in 4 h and almost all in 24 h. 10 mg/l zinc or MCA prevented most of the starch degradation for 4 h, but they did not have any effect in 24 h. When zinc and MCA were applied together, clearly better result was obtained than with either of the chemicals alone.

TABLE 1

Protection of starch from degradation using zinc and monochloramine (MCA). Two contact times, 4 and 24 h, were used. Zinc concentration is given as mg of $Zn^{2+}$ $l^{-1}$ and MCA concentrations are given as mg of active chlorine $l^{-1}$.

| Sample | Starch concentration, mg/l | |
|---|---|---|
| | 4 h | 24 h |
| Sterile control | 262 | 199 |
| Control | 44 | 7 |
| Zn 10 mg/l | 177 | 8 |
| MCA 10 mg/l | 158 | 5 |
| MCA 20 mg/l | 189 | 41 |
| MCA + Zn (10 mg/l + 10 mg/l) | 221 | 52 |
| MCA + Zn (20 mg/l + 10 mg/l) | 246 | 110 |

EXAMPLE 2

Prevention of starch degradation was studied using an oxidizing biocide (chlorine dioxide, $ClO_2$) and zinc. Head box stock from packaging board mill, stored at +4° C. after collecting, was amended with 0.8 g/l cooked starch and incubated overnight at 45° C. with 150 rpm shaking to induce the growth of starch degrading bacteria. The stock was divided into 30 ml portions and appropriate amounts of zinc ($Zn^{2+}$ from zinc chloride) and $ClO_2$ were added together with a new starch addition (400 mg/l). After 4 h and 24 h incubation (+45° C., 150 rpm) the remaining starch was quantified using iodine staining (Lugol-solution) at 590 nm. An external standard curve was used to convert absorbance values into starch amounts.

Figure 2:
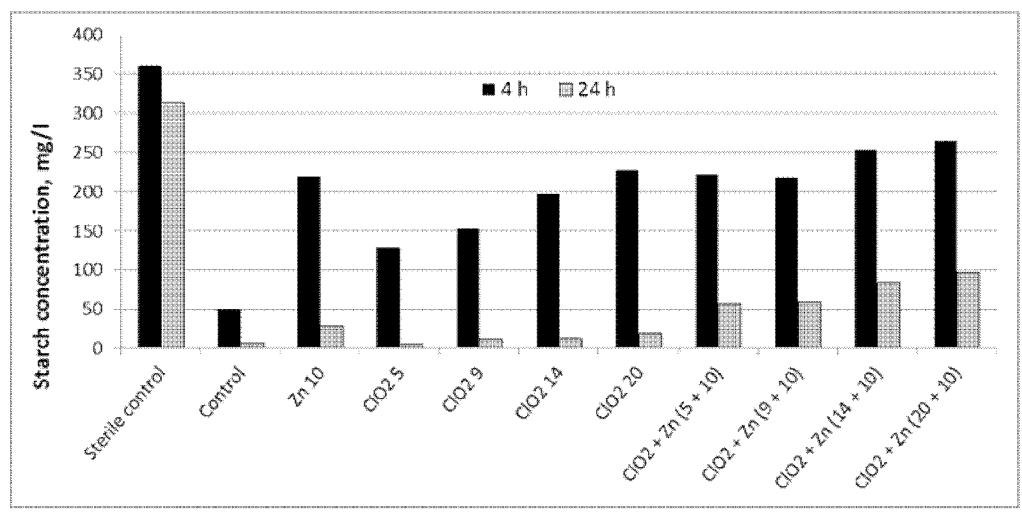
FIG. 2 shows protection of starch from degradation using zinc and chlorine dioxide ($ClO_2$), wherein two contact times, 4 h and 24 h, were used. Zinc concentration is given as mg of $Zn^{2+}$ ions per liter and $ClO_2$ concentrations are given as mg of chlorine dioxide per liter.

Table 2 hereinafter and FIG. 2 show that when no bacteria were present (sterile control) the measurable starch concentration was about 350 mg/l after 4 h and 300 mg/l after 24 h. The rest of the starch had probably retained onto fibers. In non-treated control most of the starch had been consumed already in 4 h and almost all in 24 h. 10 mg/l zinc or 5-20 mg/l $ClO_2$ prevented most of the starch degradation for 4 h, but they did not have marked effect in 24 h. When zinc and $ClO_2$ were applied together, clearly better result was obtained than with either of the chemicals alone.

TABLE 2

Protection of starch from degradation using zinc and chlorine dioxide. Two contact times, 4 and 24 h, were used. Zinc concentration is given as mg of $Zn^{2+}$ $l^{-1}$ and $ClO_2$ concentrations are given as mg of chlorine dioxide $l^{-1}$.

| Sample | Starch concentration, mg/l | |
|---|---|---|
| | 4 h | 24 h |
| Sterile control | 361 | 314 |
| Control | 50 | 6 |
| Zn 10 mg/l | 219 | 28 |
| $ClO_2$ 5 mg/l | 128 | 5 |
| $ClO_2$ 9 mg/l | 153 | 12 |
| $ClO_2$ 14 mg/l | 197 | 13 |
| $ClO_2$ 20 mg/l | 227 | 19 |
| $ClO_2$ + Zn (5 mg/l + 10 mg/l) | 221 | 57 |
| $ClO_2$ + Zn (9 mg/l + 10 mg/l) | 218 | 59 |
| $ClO_2$ + Zn (14 mg/l + 10 mg/l) | 253 | 84 |
| $ClO_2$ + Zn (20 mg/l + 10 mg/l) | 264 | 97 |

EXAMPLE 3

Prevention of starch degradation was studied using an oxidizing biocide (performic acid, PFA) and zinc. Head box stock from packaging board mill, stored at +4° C. after collecting, was amended with 0.8 g/l cooked starch and incubated overnight at 45° C. with 150 rpm shaking to induce the growth of starch degrading bacteria. The stock was divided into 30 ml portions and appropriate amounts of zinc ($Zn^{2+}$ from zinc chloride) and PFA were added together with a new starch addition (400 mg/l). After 4 h and 24 h incubation (+45° C., 150 rpm) the remaining starch was quantified using iodine staining (Lugol-solution) at 590 nm. An external standard curve was used to convert absorbance values into starch amounts.

Figure 3:
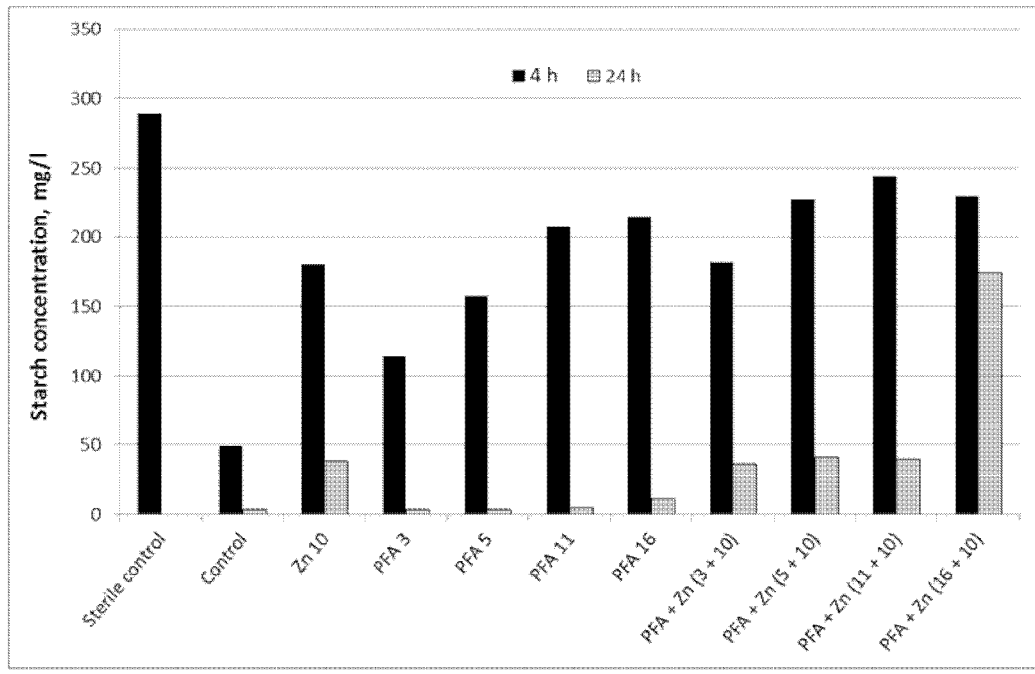
FIG. 3 shows protection of starch from degradation using zinc and performic acid (PFA), wherein two contact times, 4 h and 24 h, were used. Zinc concentration is given as mg of $Zn^{2+}$ ions per liter and PFA concentrations are given as mg of PFA (active ingredient) per liter.

Table 3 hereinafter and FIG. 3 and show that when no bacteria were present (sterile control) the measurable starch concentration was about 300 mg/l after 4 h. The rest of the starch had probably retained onto fibers. In non-treated control most of the starch had been consumed already in 4 h and almost all in 24 h. 10 mg/l zinc or 20-120 mg/l PFA prevented most of the starch degradation for 4 h, but they did not have marked effect in 24 h. When zinc and $ClO_2$ were applied together, clearly better result was obtained than with either of the chemicals alone.

TABLE 3

Protection of starch from degradation using zinc and performic acid (PFA). Two contact times, 4 and 24 h, were used. Zinc concentration is given as mg of $Zn^{2+}$ $l^{-1}$ and PFA concentrations are given as mg of PFA (active ingredient) $l^{-1}$.

| Sample | Starch concentration, mg/l | |
|---|---|---|
| | 4 h | 24 h |
| Sterile control | 289 | 0 |
| Control | 49 | 4 |
| Zn 10 mg/l | 181 | 38 |
| PFA 3 mg/l | 114 | 3 |
| PFA 5 mg/l | 157 | 3 |
| PFA 11 mg/l | 208 | 5 |
| PFA 16 mg/l | 215 | 11 |

TABLE 3-continued

Protection of starch from degradation using zinc and performic acid (PFA). Two contact times, 4 and 24 h, were used. Zinc concentration is given as mg of $Zn^{2+}$ $l^{-1}$ and PFA concentrations are given as mg of PFA (active ingredient) $l^{-1}$.

| Sample | Starch concentration, mg/l | |
|---|---|---|
| | 4 h | 24 h |
| PFA + Zn (3 mg/l + 10 mg/l) | 182 | 37 |
| PFA + Zn (5 mg/l + 10 mg/l) | 227 | 41 |
| PFA + Zn (11 mg/l + 10 mg/l) | 244 | 40 |
| PFA + Zn (16 mg/l + 10 mg/l) | 229 | 175 |

EXAMPLE 4

Prevention of starch degradation was studied using a non-oxidizing biocide (glutaraldehyde) and zinc. Head box stock from packaging board mill, stored at +4° C. after collecting, was amended with 0.8 g/l cooked starch and incubated overnight at 45° C. with 150 rpm shaking to induce the growth of starch degrading bacteria. The stock was divided into 30 ml portions and appropriate amounts of zinc ($Zn^{2+}$ from zinc chloride) and glutaraldehyde were added together with a new starch addition (400 mg/l). After 4 h and 24 h incubation (+45° C., 150 rpm) the remaining starch was quantified using iodine staining (Lugol-solution) at 590 nm. An external standard curve was used to convert absorbance values into starch amounts.

Figure 4:
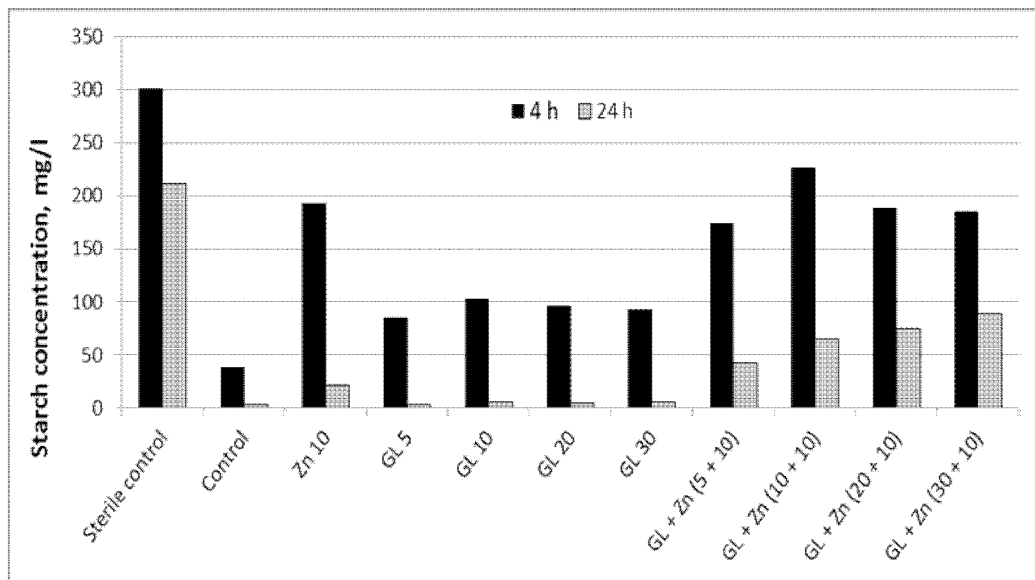
FIG. 4 shows protection of starch from degradation using zinc and glutaraldehyde, wherein two contact times, 4 h and 24 h, were used. Zinc concentration is given as mg of $Zn^{2+}$ ions per liter and glutaraldehyde concentrations are given as mg of glutaraldehyde (active substance) per liter.

Table 4 hereinafter and FIG. 4 and show that when no bacteria were present (sterile control) the measurable starch concentration was about 300 mg/l after 4 h and 200 mg/l after 24 h. The rest of the starch had probably retained onto fibers. In non-treated control most of the starch had been consumed already in 4 h and almost all in 24 h. 10 mg/l zinc or 5-30 mg/l glutaraldehyde prevented some of the starch degradation for 4 h, but they did not have marked effect in 24 h. When zinc and glutaraldehyde were applied together, clearly better result was obtained than with either of the chemicals alone.

TABLE 4

Protection of starch from degradation using zinc and glutaraldehyde. Two contact times, 4 and 24 h, were used. Zinc concentration is given as mg of $Zn^{2+}$ $l^{-1}$ and glutaraldehyde concentrations are given as mg of active substance glutaraldehyde $l^{-1}$.

| Sample | Starch concentration, mg/l | |
|---|---|---|
| | 4 h | 24 h |
| Sterile control | 301 | 212 |
| Control | 39 | 3 |
| Zn 10 mg/l | 193 | 21 |
| GL 5 mg/l | 85 | 3 |
| GL 10 mg/l | 103 | 5 |
| GL 20 mg/l | 96 | 4 |
| GL 30 mg/l | 93 | 6 |
| GL + Zn (5 mg/l + 10 mg/l) | 174 | 42 |
| GL + Zn (10 mg/l + 10 mg/l) | 227 | 65 |
| GL + Zn (20 mg/l + 10 mg/l) | 189 | 75 |
| GL + Zn (30 mg/l + 10 mg/l) | 185 | 89 |

The examples show that biocidal systems according to the invention provide superior effects in terms of preventing starch degradation in starch-containing process waters.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following embodiments.

Preferred embodiments of the invention are described hereinafter.

Embodiments

1. A biocidal composition comprising zinc ions and a biocide, wherein the non-oxidizing biocide does not include zinc pyrithione or 1,2-benzoisothiazolin-3-one and zinc pyrithione.
2. The biocidal composition of embodiment 1, wherein the biocide is an oxidizing biocide or a non-oxidizing biocide.
3. The biocidal composition of embodiment 1, wherein the zinc ions are derived from an inorganic or organic zinc salt.
4. The biocidal composition of embodiment 3, wherein the inorganic or organic zinc salt can be selected from: $ZnBr_2$, $ZnCl_2$, $ZnF_2$, $ZnI_2$, $ZnO$, $Zn(OH)_2$, $ZnS$, $ZnSe$, $ZnTe$, $Zn_3N_2$, $Zn_3P_2$, $Zn_3As_2$, $Zn_3Sb_2$, $ZnO_2$, $ZnH_2$, $ZnC_2$, $Zn(NO_3)_2$, $Zn(ClO_3)_2$, $ZnSO_4$, $Zn_3(PO_4)_2$, $ZnMoO_4$, $ZnCrO_4$, $Zn(AsO_2)_2$, $Zn(AsO_4)_2$, $Zn(O_2CCH_3)_2$, zinc metal, and a combination thereof.
5. The biocidal composition of embodiment 1, wherein the non-oxidizing biocides are selected from: glutaraldehyde, 2,2-dibromo-3-nitrilopropionamide (DBNPA), 2-bromo-2-nitropropane-1,3-diol (Bronopol), quaternary ammonium compounds, carbamates, 5-chloro-2-methyl-4-isothiazolin-3-one (CMIT), 2-methyl-4-isothiazolin-3-one (MIT), 1,2-dibromo-2,4-dicyanobutane, bis(trichloromethyl)sulfone, 2-bromo-2-nitro styrene, 4,5-dichloro-1,2-dithiol-3-one, 2-n-octyl-4-isothiazolin-3-one, 1,2-benzisothiazolin-3-one, orthophthaldehyde, quaternary ammonium compounds (="quats"), guanidines, biguanidines, pyrithiones, 3-iodopropynyl-N-butylcarbamate, tetrakis hydroxymethyl phosphonium sulfate (THPS), dazomet, 2-(thiocyanomethylthio) benzothiazole, methylene bisthiocyanate (MBT), and a combination thereof.
6. The biocidal composition of embodiment 1, wherein the oxidizing biocides are selected from: chlorine, alkali and alkaline earth hypochlorite salts, hypochlorous acid, chlorinated isocyanurates, bromine, alkali and alkaline earth hypobromite salts, hypobromous acid, bromine chloride, chlorine dioxide, ozone, hydrogen peroxide, peroxy compounds, halogenated hydantoins, and a combination thereof.

7. A method of preventing or reducing the amount of starch degradation, comprising:
    treating the fluid that includes starch with zinc ions and a biocide.
8. The method of embodiment 7, wherein the biocide is an oxidizing biocide or a non-oxidizing biocide.
9. The method of embodiment 7, wherein the zinc ions are derived from an inorganic or organic zinc salt.
10. The method of embodiment 9, wherein the inorganic or organic zinc salt can be selected from: $ZnBr_2$, $ZnCl_2$, $ZnF_2$, $ZnI_2$, $ZnO$, $Zn(OH)_2$, $ZnS$, $ZnSe$, $ZnTe$, $Zn_3N_2$, $Zn_3P_2$, $Zn_3As_2$, $Zn_3Sb_2$, $ZnO_2$, $ZnH_2$, $ZnC_2$, $Zn(NO_3)_2$, $Zn(ClO_3)_2$, $ZnSO_4$, $Zn_3(PO_4)_2$, $ZnMoO_4$, $ZnCrO_4$, $Zn(AsO_2)_2$, $Zn(AsO_4)_2$, $Zn(O_2CCH_3)_2$), zinc metal, and a combination thereof.
11. The method of embodiment 7, wherein the non-oxidizing biocides are selected from: glutaraldehyde, 2,2-dibromo-3-nitrilopropionamide (DBNPA), 2-bromo-2-nitropropane-1,3-diol (Bronopol), quaternary ammonium compounds, carbamates, 5-chloro-2-methyl-4-isothiazolin-3-one (OMIT), 2-methyl-4-isothiazolin-3-one (MIT), 1,2-dibromo-2,4-dicyanobutane, bis(trichloromethyl)sulfone, 2-bromo-2-nitrostyrene, 4,5-dichloro-1,2-dithiol-3-one, 2-n-octyl-4-isothiazolin-3-one, 1,2-benzisothiazolin-3-one, orthophthaldehyde, quaternary ammonium compounds (="quats"), guanidines, biguanidines, pyrithiones, 3-iodopropynyl-N-butylcarbamate, tetrakis hydroxymethyl phosphonium sulfate (THPS), dazomet, 2-(thiocyanomethylthio) benzothiazole, methylene bisthiocyanate (MBT), and a combination thereof.
12. The method of embodiment 7, wherein the oxidizing biocides are selected from: chlorine, alkali and alkaline earth hypochlorite salts, hypochlorous acid, chlorinated isocyanurates, bromine, alkali and alkaline earth hypobromite salts, hypobromous acid, bromine chloride, chlorine dioxide, ozone, hydrogen peroxide, peroxy compounds, halogenated hydantoins, and a combination thereof.
13. A method of inhibiting existing amylase activity, comprising:
    treating a with zinc ions and a biocide.
14. A method of preventing or reducing the production of new amylase by microorganisms, comprising:
    treating a with zinc ions and a biocide.
15. A method of inhibiting existing amylase activity and preventing or reducing the production of new amylase by microorganisms, comprising:
    treating a with zinc ions and a biocide.

The invention claimed is:
1. A method of controlling starch degradation in starch-containing process water from pulp, paper or board production, comprising:
    treating the process water with zinc ions and a biocide, wherein the zinc ions and the biocide is an oxidizing biocide.
2. The method of claim 1, wherein the zinc ions and the biocide are continuously, intermittently or alternately added to the starch-containing process water.
3. The method of claim 1, wherein the zinc ions and the biocide are added simultaneously to the starch-containing process water.
4. The method of claim 1, wherein the biocide is added prior to the addition of the zinc ions.
5. The method of claim 1, wherein the zinc ions are added prior to the addition of the biocide.

* * * * *